United States Patent
Plotnikov et al.

(10) Patent No.: US 6,720,775 B2
(45) Date of Patent: Apr. 13, 2004

(54) PULSED EDDY CURRENT TWO-DIMENSIONAL SENSOR ARRAY INSPECTION PROBE AND SYSTEM

(75) Inventors: Yuri Alexeyevich Plotnikov, Niskayuna, NY (US); Shridhar Champaknath Nath, Niskayuna, NY (US); Curtis Wayne Rose, Mechanicville, NY (US); Thomas James Batzinger, Burnt Hills, NY (US); Kenneth Gordon Herd, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/681,824

(22) Filed: Jun. 12, 2001

(65) Prior Publication Data

US 2002/0190724 A1 Dec. 19, 2002

(51) Int. Cl.[7] .................. G01R 31/28; G01R 33/12; G01N 27/82
(52) U.S. Cl. .................. 324/529; 324/238; 324/242
(58) Field of Search ............... 324/529, 238, 324/242

(56) References Cited

U.S. PATENT DOCUMENTS

| | | | | |
|---|---|---|---|---|
| 3,875,502 A | | 4/1975 | Neumaier | 324/241 |
| 4,292,589 A | * | 9/1981 | Bonner | 324/221 |
| 4,495,466 A | * | 1/1985 | Lakin | 324/228 |
| 5,056,049 A | * | 10/1991 | O'Neill | 340/623 |
| 5,391,988 A | | 2/1995 | Kitagawa | 324/225 |
| 5,434,506 A | * | 7/1995 | Flora | 324/233 |
| 5,491,409 A | * | 2/1996 | Flora et al. | 324/235 |
| 5,659,248 A | | 8/1997 | Hendengren et al. | 324/242 |
| 6,037,768 A | | 3/2000 | Moulder et al. | 324/225 |
| 6,124,712 A | | 9/2000 | Chaiken | 324/326 |
| 6,150,809 A | * | 11/2000 | Tiernan et al. | 324/225 |
| 6,259,826 B1 | * | 7/2001 | Pollard et al. | 358/450 |
| 6,344,741 B1 | | 2/2002 | Giguere et al. | |
| 6,366,085 B1 | * | 4/2002 | Yeshurun et al. | 324/235 |

FOREIGN PATENT DOCUMENTS

| | | |
|---|---|---|
| EP | 0533440 A | 2/1995 |
| EP | 0512796 B | 8/1997 |

OTHER PUBLICATIONS

R. Rempt, Scanning with Magnetoresistive Sensors for Subsurface Corrosion, D.O. Thompson & D.E. Chimenti (Eds.), Review of Progress in QNDE, vol. 21B, AIP, N.Y., 2002, pp. 1771–1778.

Y.A. Plotnikov, S.C. Nath, and C.W. Rose, Defect Characterization in Multi–Layered Conductive Components with Pulsed Eddy Current, D. O. Thompson and D.E. Chimenti (Eds.), Review of Progress in QNDE, vol. 21B, AIP, N.Y., 2002, pp. 1976–1983.

European Search Report, Application Number EP 02 25 4028, The Hague, Oct. 24, 2003.

* cited by examiner

*Primary Examiner*—N. Le
*Assistant Examiner*—John Teresinski
(74) *Attorney, Agent, or Firm*—Penny A. Clarke; Patrick K. Patnode

(57) ABSTRACT

A pulsed eddy current two-dimensional sensor array probe for electrically conducting component inspection includes a drive coil disposed adjacent to a structure under inspection, a pulse generator connected to the drive coil and operable to energize in a pulsed manner the drive coil to transmit transient electromagnetic flux into the structure under inspection, and an array of sensors arranged in a two-dimensional array and substantially surrounded by the drive coil and operable to sense and generate output signals from the transient electromagnetic flux in the structure under inspection.

16 Claims, 4 Drawing Sheets

PULSED EDDY CURRENT TWO-DIMENSIONAL SENSOR ARRAY INSPECTION PROBE AND SYSTEM

BACKGROUND OF INVENTION

The present invention generally relates to nondestructive evaluation of metallic structures and, more particularly, is concerned with a pulsed eddy current two-dimensional sensor array probe and system for electrically conducting component inspection.

The presence of surface cracks and subsurface flaws in metallic structures, such as aircraft skin structures, have the potential to lead to catastrophic failure. Various inspection methods have been used heretofore for crack and flaw detection with varying degrees of success.

One prior art inspection method uses eddy current probes which can give an indication of depth to ascertain crack and flaw severity. The probes requires close contact with the part and have limited resolution and inspection speed. Also, complicated contour following is needed to inspect curvatures of some parts. Lift off between the probes and the part is a major concern. Full coverage with eddy current probes is very time consuming, which leads to spot checking which may miss critical crack and defect areas.

Consequently, a need still exists for an innovation which will provides a solution to the aforementioned problem without introducing any new problems in place thereof.

SUMMARY OF INVENTION

The present invention provides a pulsed eddy current two-dimensional sensor array probe, system and data visualization for electrically conducting component inspection designed to satisfy the aforementioned need. The probe uses a two-dimensional array of magnetic field sensors for inspection of electrically conducting components without requiring mechanical scanning. A coil (solenoid) is used to transmit an electromagnetic pulse of a fixed duration into a component. The induced eddy current penetrates the structure and serves to produce a pattern of electromagnetic transient field above a defect. The two-dimensional array of sensors is located in a plane within the drive coil. Static scanning is employed to collect time evolution response of the magnetic field from all the sensors. This is performed by electronically switching the sensors while the probe is placed in a stationary position on the conducting structure. The response from the sensors is processed to determine the material thickness with a two-dimensional map representing a full field of view.

In one embodiment of the present invention, a pulsed eddy current two-dimensional sensor array probe for electrically conducting component inspection is provided which comprises a drive coil disposed adjacent to a structure under inspection, a pulse generator connected to the drive coil and operable to energize in a pulsed manner the drive coil to transmit transient electromagnetic flux into the structure under inspection, and an array of sensors arranged in a two-dimensional array and substantially surrounded by the drive coil and operable to sense and generate output signals from the transient electromagnetic flux in the structure under inspection.

In another embodiment of the present invention, a pulsed eddy current two-dimensional sensor array system for electrically conducting component inspection is provided which comprises a pulsed eddy current two-dimensional sensor array probe for transmitting in a pulsed manner a transient electromagnetic flux into a structure under test and for sensing and generating output signals from the transient electromagnetic flux in the structure under inspection, and a data acquisition apparatus for receiving and processing the output signals and outputting the processed signals in the form of a two-dimensional image made up of pixels that correspond to the array of sensors. The two-dimensional image is formed by a given gray level to the amplitude of an informative parameter that is computed for each individual sensor in the two-dimensional array. Each element (pixel) of the image is located according to the spatial position of the sensor in the array.

DETAILED DESCRIPTION

Figure 1:
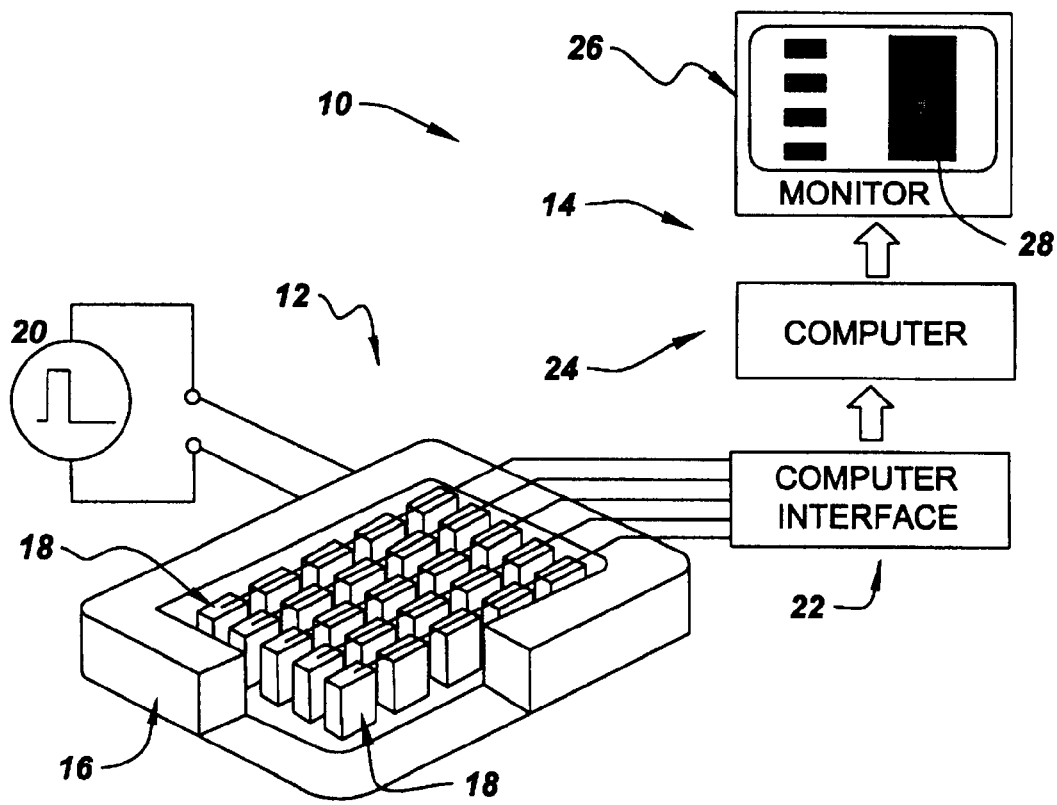
FIG. 1 is a diagrammatic representation of a pulsed eddy current two-dimensional sensor array inspection probe and system of the present invention.

Referring now to the drawings, and particularly to FIG. 1, there is diagrammatically illustrated an eddy current-based nondestructive inspection system, generally designated 10, of the present invention used for nondestructive evaluation of metallic structures, such as aircraft skin structures, for detection and visualization of surface cracks and subsurface flaws. The inspection system 10 generally includes a pulsed eddy current two-dimensional sensor array probe, generally designated 12, and a data acquisition apparatus, generally designated 14.

The pulsed eddy current two-dimensional sensor array probe 12 includes a drive coil 16, an array of sensors 18 arranged in a two-dimensional array, and a square pulse generator 20. The data acquisition apparatus 14 includes a computer interface 22, a computer 24, such as a personal computer, and a computer monitor 26. The drive coil 16 is a multiple-turn solenoid of generally rectangular configuration surrounding the array of sensors 18. The rectangular drive coil 16 is used for transmitting a transient electromagnetic flux into a structure under test.

The array of sensors 18 forms a rectangular matrix inside the drive coil 16. The pulse generator 20 is used to excite the rectangular drive coil 16 with a square-shaped short duration pulse of electrical current. The computer interface 22 provides multiplexing of the responses from the bank of sensors 18 and communicates the digitized signals into the computer 24. Customized software stored in the computer 24 processes the acquired data and displays the results on a monitor 26 of the computer 24 in the form of a two-dimensional image 28 where each pixel represents a result of data processing of the corresponding sensor 18. Using the computer 24, a wide variety of digital image processing methods can be used to obtain better representation of a flaw.

Figure 2:
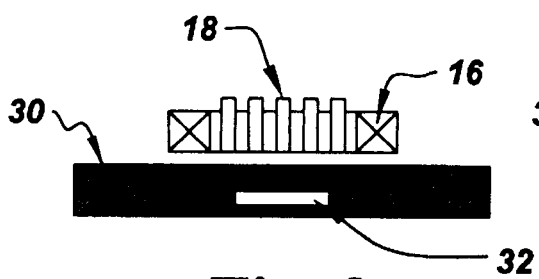
FIGS. 2 to 5 are diagrammatic representations of several different mutual locations of the sensors and the drive coil in the array probe
Figure 3:
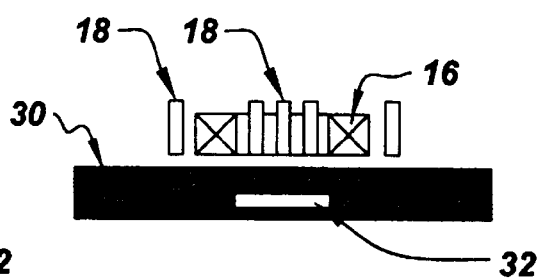
Figure 4:
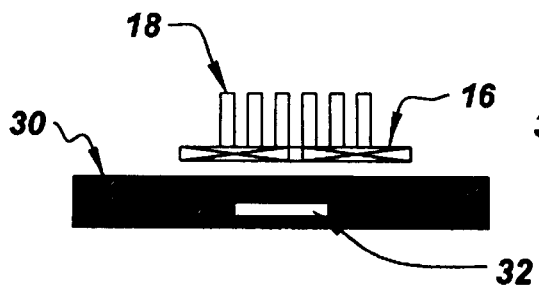
Figure 5:
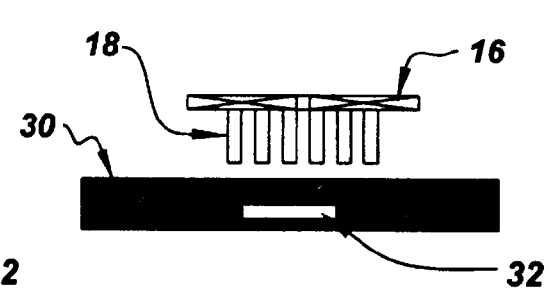

Sensors 18 can be located inside or outside as well as above or below the drive coil 16. Particularly, FIGS. 2 to 5 demonstrate four different settings of a drive coil and sensors that were tested for the purpose of the present invention. In FIG. 2 a two-dimensional array of sensors 18 is placed inside of the rectangular drive coil 16. In FIG. 3, a two-dimensional array of sensors 18 is placed inside the drive coil 16 and two additional one-dimensional arrays of sensors are placed outside of the rectangular drive coil 16. Two probe configurations with a flat drive coil of pancake or spiral type are shown in FIGS. 4 and 5. FIG. 4 depicts a case where the sensors 18 are placed on top of the drive coil 16, while FIG. 5 represents a case where the sensors are placed under the drive coil 16, closer to the surface of an inspected component 30.

Probes 12 of different size and number of sensors 18 in the array can be fabricated depending on the particular application. For example, a drive coil 16 with internal dimensions of 13 mm×66 mm and external dimensions of 26 mm×79 mm having 260 turns of AWG 30 wire has been fabricated and evaluated. Array of 3×8 GMR sensors was placed inside and two arrays of 1×8 GMR sensors were placed outside of the drive coil 16 as in the setting shown in FIG. 3. The probe 12 was placed over a structure that consists of two layers of 1.6 mm thick aircraft aluminum. A 2 A square pulse with duration of twenty microseconds is used to excite the drive coil 16.

Figure 6:
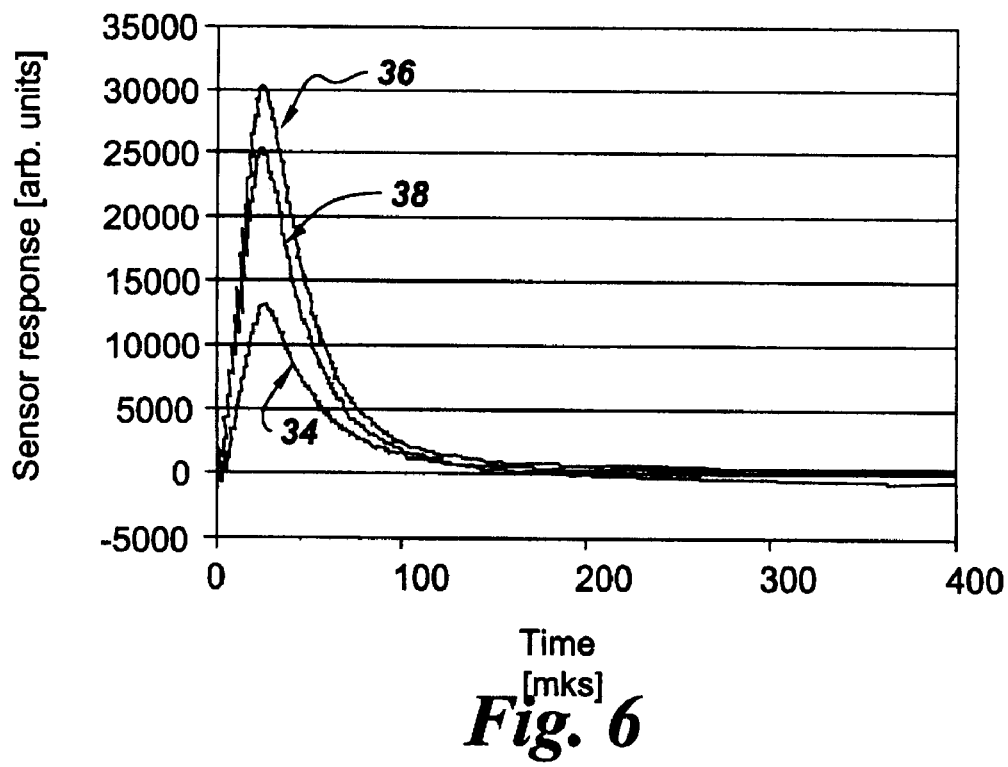
FIG. 6 is a graph depicting transient signals from the sensors located within and outside of a drive coil obtained during evaluation of the probe of the present invention while the probe was placed over a flawless region.

The time evolution signals from the sensors 18 were digitized with a sampling frequency of 2.5 MHz. Typical signals obtained from the GMR sensors for a period of 400 microseconds while the probe 12 was positioned over a flawless region are presented in FIG. 6. Magnitude of the sensor response rises during the time when the current is on and drops to the initial value after the end of the drive pulse. Curve 34 is a signal obtained from a GMR sensor that is located at the center of the probe 12, curves 36 and 38 were obtained from the sensors that are located next to the wound wires inside and outside of the coil 16 respectively. Because of variable proximity to the drive coil wires, the significant variations of the responses from the sensors 18 have been observed. A reference signal recording for every sensitive element in the array may be employed to eliminate these variations.

A transient electromagnetic signal obtained from the sensor 18 depends on its position inside or outside the drive coil 16 and the geometry of the component directly under this sensor 18. Nulling of the probe is made on a flawless region of the component to record into the computer memory the transient responses from each sensor 18. During inspection, the response signal is subtracted from the signal obtained for this sensor 18 during the nulling phase. The signal differences after the end of the exciting pulse that have been obtained from the GMR sensors while the probe 12 was positioned over a flaw are presented in FIG. 7. The flaw was simulated by a 19 mm in diameter flat bottom hole 0.35 mm deep. The hole is positioned on the top of the second layer of the specimen as shown in FIG. 3. Curve 40 is a signal difference obtained from a GMR sensor that is located over the center of the flaw. Curve 42 is a signal difference obtained from a GMR sensor that is located over the edge of the flaw. Curve 44 is a signal difference obtained from a GMR sensor that is located over flawless region. The variations between the signal differences from the sensors 18 located in the probe 12 differently in respect to the flaw allow forming an image of the flaw.

A two-dimensional image 28 is formed by giving a gray level to the amplitude of an informative parameter that is computed for each individual sensor in the two-dimensional array. Each element (pixel) of the image is located according to the spatial position of the sensor in the array. Using a color map (also called a color palette), a color image is formed as the color values are given to each pixel of the gray scale image from the corresponding look-up tables.

A wide variety of algorithms can be used to compute the informative parameter for the sensors. For example, the informative parameter S that can be used to form an image is the mean of the signal difference U during a fixed time interval $t_1-t_2$:

$$S(i, j) = \frac{1}{N} \sum_{n=1}^{N} U(i, j, n), \quad (1)$$

where i and j are the coordinates of the sensors 18 in the two-dimensional array and N is the number of sampled values of the signal difference U(i,j,n) during the time interval $t_1-t_2$.

Alternatively, the informative parameter S can be computed by using a sine filter by convolving the signal difference U(i,j,n) with the sin( ) function:

$$S(i, j) = \frac{1}{N} \sum_{n=1}^{N} U(i, j, n) \sin\left(\frac{2\pi \cdot (n-1)}{N}\right). \quad (2)$$

Since the informative parameter S defined by the equation (2) is not sensitive to the constant level bias of the signal U, this algorithm was found to be effective in presence of an external magnetic field with constant level during the measurement cycle. Generally, most of the known discrete transforms (Fourier, Laplace, wavelet, etc.) applied in the time domain can be used to compute the informative parameter S.

Figure 7:
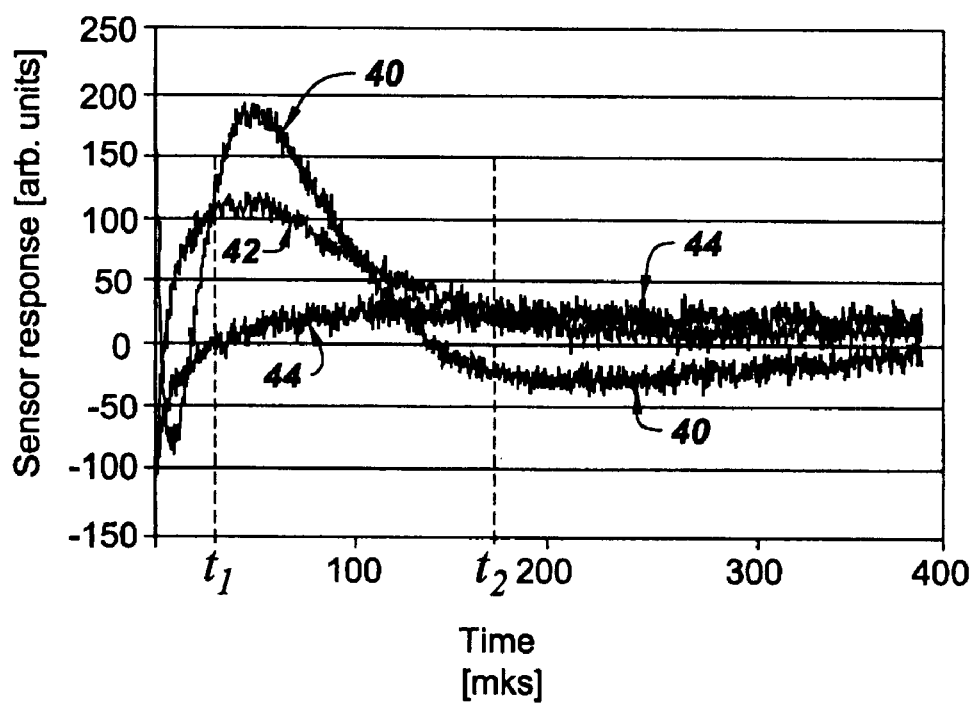
FIG. 7 is a graph depicting signal differences from the sensors within a drive coil of the probe of the present invention while the probe was placed over a flat bottom hole.
Figure 8:
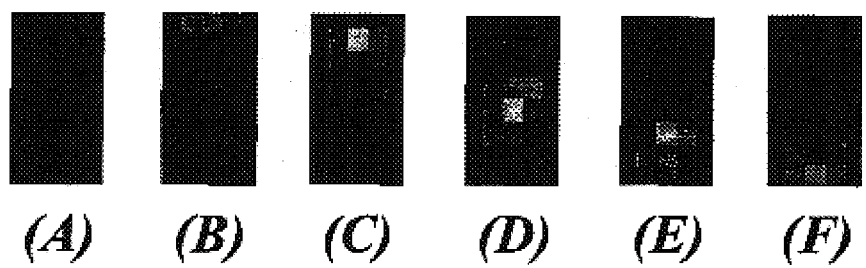
FIG. 8 is a set of two-dimensional images obtained with an array of 5×8 sensors while the probe of the present invention passes over a flat bottom hole.

FIG. 8 depicts the images (a) (f) that have been obtained from the above described setup by using equation (2) for informative parameter computations. The image (a) was obtained while the probe was placed over flawless region. The images (b) (f) were obtained while the probe passed over the simulated flaw (flat bottom hole 32). As can be seen in FIG. 7, a choice of the time interval $t_1-t_2$ is pertinent to the flaw detection. The time interval from $t_1=8$ μs to $t_2=320$ μs beyond the drive pulse was found to be suitable for detecting the simulated flaw when it is located on the top of the second layer of the specimen as shown in FIG. 3.

Customized software stored in the computer 24 controls the data acquisition, processes the acquired data and displays the results on a monitor 26. Pulse generator 20 produces current pulses through the drive coil 16 with a repetition rate of 100 Hz. The electronic switching the sensor outputs by row and column is made by means of computer interface 22 after completion of data collection cycle for each sensor. In the setup used, based on a personal computer with 200 MHz processor and developed software, the images were updated two times per second. This arrangement provides real-time monitoring of a component under test. The images can be updated faster or slower depending on the used software program and computer hardware.

In the above described example, GMR sensors were used as the magnetic field sensors 18. Alternatively, other magnetic field sensors such as wound coil sensors, Hall elements, flux gate sensors, etc. can also be used. As an alternative to an array of discrete elements fabricated individually, an array of sensors 18 can be performed as one integral module using eddy current array probe (ECAP) technology or integral circuit technology.

Productivity and turnaround time are the drivers in today's economic environment. The array of sense elements, such as Giant Magnetoresistive (GMR) detectors, wound and deposited coils, flux gate sensors or Hall elements, combined with pulsed electromagnetic excitation provides the competitive edge. Also, the two-dimensional representation is much more informative and provides a real-time visual representation of the flaws in the structure under test.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

What is claimed is:

1. A pulsed eddy current inspection system comprising:
   an eddy current probe comprising a two-dimensional array of sensors and being configured to transmit in a pulsed manner transient electromagnetic flux into a structure under test and further being configured to output signals from the transient electromagnetic flux in the structure under test, said two-dimensional array of sensors comprising a plurality of sensors; and
   a data acquisition apparatus configured to receive the output signals, said data acquisition apparatus being further configured to process the output signals using an informative parameter to generate a two-dimensional image, wherein an amplitude of the informative parameter assumes a plurality of values, each of the values of the amplitude of the informative parameter being associated with a respective one of said sensors, and said data acquisition apparatus being further configured to output the two-dimensional image comprising a plurality of pixels that correspond to said two-dimensional array of sensors.

2. The system of claim 1, wherein said eddy current probe further comprises a drive coil disposed adjacent to the structure under inspection, said drive coil being configured to transmit in a pulsed manner transient electromagnetic flux into the structure under test.

3. The system of claim 2, wherein said drive coil is a multiple-turn solenoid substantially surrounding said two-dimensional array of sensors.

4. The system of claim 2 in which said drive coil has a generally rectangular configuration.

5. The system of claim 2 in which said probe further includes a pulse generator connected-to said drive coil and operable to energize said drive coil to transmit a transient electromagnetic flux into the structure under inspection.

6. The system of claim 5 in which said pulse generator is a square wave pulse generator.

7. The system of claim 5, wherein said two-dimensional array is disposed adjacent to said drive coil and operable to sense and generate output signals from the transient electromagnetic flux in the structure under inspection.

8. The system of claim 7 in which said array of sensors form a rectangular matrix within said drive coil.

9. The system of claim 1, wherein said data acquisition apparatus includes:
   a computer configured to process the output signals using the informative parameter to generate the two-dimensional image ; and
   a computer interface interconnecting said two-dimensional array of sensors to said computer.

10. The system of claim 1, wherein said data acquisition apparatus assigns a gray level to each of the pixels, each gray level corresponding to the amplitude of the informative parameter for a respective one of said sensors.

11. The system of claim 9, wherein said computer interface is configured to multiplex the output signals from said two-dimensional array of sensors, and wherein said computer interface is further configured to communicate data in the form of digitized signals to said computer.

12. The system of claim 9, wherein said computer includes a monitor, said computer being operable to output a plurality of signals corresponding to the two-dimensional image to and display the results on said monitor.

13. The system of claim 9, wherein said computer assigns a gray level to each of the pixels, each gray level corresponding to the amplitude of the informative parameter for a respective one of said sensors.

14. The system of claim 9, wherein said computer is further configured to compute a value of the amplitude of the informative parameter for each of the sensors.

15. The system of claim 14, wherein said computer is further configured to assign a gray level to each of the pixels, each gray level corresponding to the amplitude of the informative parameter for a respective one of said sensors.

16. The system of claim 15, wherein said computer is configured to generate a two-dimensional color image by assigning a color value selected from a color map to each of the pixels based on the gray value assigned to the respective one of the pixels.

* * * * *